United States Patent
Young et al.

(10) Patent No.: US 11,484,212 B2
(45) Date of Patent: Nov. 1, 2022

(54) SYSTEMS AND METHODS FOR MONITORING ANIMAL VITALS

(71) Applicant: SKYPAWS, INC., Levelland, TX (US)

(72) Inventors: Stephanie Kay Young, Levelland, TX (US); Brianna E. Armstrong, College Station, TX (US)

(73) Assignee: SKYPAWS, Inc., Levelland, TX (US)

( * ) Notice: Subject to any disclaimer, the term of this patent is extended or adjusted under 35 U.S.C. 154(b) by 0 days.

(21) Appl. No.: 16/595,407

(22) Filed: Oct. 7, 2019

(65) Prior Publication Data

US 2020/0107734 A1 Apr. 9, 2020

Related U.S. Application Data

(60) Provisional application No. 62/742,202, filed on Oct. 5, 2018.

(51) Int. Cl.
*A61B 5/0205* (2006.01)
*A61B 5/00* (2006.01)
(Continued)

(52) U.S. Cl.
CPC ........ *A61B 5/02055* (2013.01); *A61B 5/0002* (2013.01); *A61B 5/01* (2013.01); *A61B 5/14551* (2013.01); *A61B 5/318* (2021.01); *A61B 5/742* (2013.01); *A61B 5/7405* (2013.01); *A61B 5/746* (2013.01); *A61B 5/748* (2013.01); *A61B 5/7455* (2013.01); *G08B 7/06* (2013.01);
(Continued)

(58) Field of Classification Search
CPC ..... A61B 5/02055; A61B 5/0002; A61B 5/01; A61B 5/0402; A61B 5/14551; A61B 5/7405; A61B 5/742; A61B 5/7455; A61B 5/746; A61B 5/748; A61B 5/02438; A61B 5/0816; A61B 2503/40; G16H 10/60; G08B 7/06
See application file for complete search history.

(56) References Cited

U.S. PATENT DOCUMENTS 6,113,539 A * 9/2000 Ridenour ............. A61B 5/0002
128/903
9,615,547 B2 4/2017 Menkes et al.
(Continued)

FOREIGN PATENT DOCUMENTS

EP 1579804 A1 9/2005
GB 2162325 A 1/1986

OTHER PUBLICATIONS

International Search Report and Written Opinion dated Jan. 16, 2020 for International Application No. PCT/US2019/055076.

*Primary Examiner* — Jonathan T Kuo
*Assistant Examiner* — Vynn V Huh
(74) *Attorney, Agent, or Firm* — Jordan IP Law, LLC; Todd A. Vaughn

(57) ABSTRACT

A system for monitoring animal vitals can include a housing, a controller and one or more sensors for sensing vital signs. The housing can be configured to couple to one or more locations on an animal. A system can be adapted for monitoring two or more vital signs simultaneously and for conveying vital sign information to a user. A system can be adapted for alerting a user to the presence or absence of one or more conditions. A system can include a plurality of sensor units and can be adapted for monitoring a plurality of patients simultaneously.

11 Claims, 11 Drawing Sheets

(51) Int. Cl.
- *A61B 5/01* (2006.01)
- *A61B 5/1455* (2006.01)
- *A61B 5/318* (2021.01)
- *G08B 7/06* (2006.01)
- *G16H 10/60* (2018.01)
- *A61B 5/024* (2006.01)
- *A61B 5/08* (2006.01)
- *A61B 5/332* (2021.01)
- *G16H 40/67* (2018.01)
- *G08B 21/04* (2006.01)
- *G16H 50/20* (2018.01)

(52) U.S. Cl.
CPC .......... *G16H 10/60* (2018.01); *A61B 5/02438* (2013.01); *A61B 5/0816* (2013.01); *A61B 2503/40* (2013.01)

(56) References Cited

U.S. PATENT DOCUMENTS

| | | |
|---|---|---|
| 2002/0154015 A1 | 10/2002 | Hixson |
| 2007/0255124 A1* | 11/2007 | Pologe ................. A61B 5/7475 600/331 |
| 2012/0059664 A1* | 3/2012 | Georgiev ................. A61B 5/02 705/2 |
| 2014/0123912 A1* | 5/2014 | Menkes ............. A61B 5/02055 119/859 |
| 2015/0148622 A1* | 5/2015 | Moyer ................. A61B 5/0059 600/301 |
| 2015/0157435 A1* | 6/2015 | Chasins ................... A61B 5/01 600/301 |
| 2017/0127975 A1* | 5/2017 | Bozkurt ................ A01K 29/005 |
| 2018/0035953 A1* | 2/2018 | Quinn .................... G16H 20/30 |
| 2018/0132735 A1* | 5/2018 | Weebadde ............... A61B 5/01 |
| 2019/0110684 A1* | 4/2019 | Coen .................. A61B 5/0255 |

* cited by examiner

≡ SkyPaws Dashboard Devices Wiki     Shaylee ⚙ ⤴

↙ 162

Q Search Everything

Display Settings <u>Last Visited</u> ⌄
   Sorting Data by Last Visited

✿ Beethoven   Jeff F. Gibbons
Last Visit: Monday, November 12th 2018   (BPM-82) (SP02-99%) (Healthy ECG)
                                                          ⏞ 156
More Information ^   Contact Owner     BPM    SP02    ECG ✿ Logan   Jason E. Patrick
Last Visit: Thrusday, November 2nd 2018   (BPM-92) <u>(SP02-88%)</u> (Healthy ECG) ← 164
More Information ^   Contact Owner     BPM    SP02    ECG    ← 164

✿ Fluffy   Juanita R. Hoffman
Last Visit: Friday, August 25th 2018   (BPM-55) (SP02-98%) (Healthy ECG)
(×)(=)(▶) More Information ^   Contact Owner     BPM    SP02    ECG

FIG. 7

SkyPaws Dashboard  Devices  Wiki  Shaylee

162

Search Everything

Display Settings
- Reverse Alphabetical by Pet Name
- Alphabetical by Owner Name
- Reverse Alphabetical by Owner Name
- Healthy BMP
- Below Healthy BMP
- Healthy SPO2

Beethoven Je...
Last Visit: Monda...
More Information

Logan Jason E. Patrick
Last Visit: Tuesday, November 2nd 2018  Contact Owner
More Information ˄   BPM-92   SP02-98%   Healthy ECG — 156
                         164      164
                         BPM      SP02      ECG

| Details | BPM | SP02 | ECG | Contact |
|---------|-----|------|-----|---------|
|         |     |      |     |         |

⚠ Jason E. Patrick Has Recieved a Low SP02 Message!  Message  Undo  ~172

Pet SP02

Enter the Lower Acceptable Range   Lower Range
                                    %90

Enter the Upper Acceptable Range   Upper Range
                                    %100

[Update Values]

SP02 Readings

Current                  88%
                         SP02 is Currently Unhealthy  ⎫
                                                      ⎬ ~156
9/15/2018 - 12/1/2018    92% - 100%                   ⎪
                         Overall SP02 Range.          ⎭

9/15/2018                SP02 Sensor Inserted

SYSTEMS AND METHODS FOR MONITORING ANIMAL VITALS

CROSS REFERENCE TO RELATED APPLICATIONS

This application claims the benefit of U.S. Provisional Patent Application No. 62/742,202 filed Oct. 5, 2018, the entire contents of which are hereby incorporated by reference into this application.

BACKGROUND OF THE INVENTION

1. Field of the Invention

The present disclosure relates generally to the field of medical devices and more specifically relates to devices for monitoring animal vital signs.

2. General Background

Veterinarians, their technicians and other personnel are often tasked with the important role of nursing animals back to health or even saving their lives. Monitoring a patient's vital signs is a fundamental part of medical care, particularly when there is reason to believe that one or more of the patient's essential body functions may be in jeopardy. Response time can be crucial, especially in life or death situations, and thus knowing that a problem exists as quickly as possible can be of the utmost importance.

In a veterinary setting in particular, unique obstacles to speedy and accurate information can exist as compared to the medical treatment of people because the patients cannot speak and otherwise have little or no ability to communicate the nature of a medical issue to a doctor in many cases. In addition, pets and other animals are often placed in kennels or other areas before and/or after treatment where direct human monitoring may be unavailable or sporadic.

Accordingly, a need exists in the art for improved devices, systems and methods for monitoring animal vital signs and for providing veterinarians and others with improved tools for saving lives.

The present disclosure is directed to devices, systems and methods for monitoring vitals, such as canine vitals, and alerting veterinary or other personnel when and if an animal is or may be going into or approaching one or more medical conditions, such as cardiac arrest, which can facilitate the timeliness of resuscitation or other medical efforts for improving an animal's chances for survival.

BRIEF SUMMARY OF THE INVENTION

A system for monitoring animal vitals can include a housing, a controller and one or more sensors for sensing vital signs. The housing can be configured to couple to one or more locations on an animal. A system can be adapted for monitoring two or more vital signs simultaneously and for conveying vital sign information to a user. A system can be adapted for alerting a user to the presence or absence of one or more conditions. A system can include a plurality of sensor units and can be adapted for monitoring a plurality of patients simultaneously.

In at least one embodiment, a system can include a housing having a first side and a second side, a controller disposed within the housing, and at least one sensor operably coupled to the controller and disposed at least partially within the housing, wherein the housing is configured to be coupled to an animal, wherein the second side of the housing is configured to be disposed in direct contact with the animal's skin, wherein the at least one sensor is operably coupled with the second side of the housing, and wherein the at least one sensor is configured to sense at least one vital sign.

In at least one embodiment, the at least one sensor can include a plurality of sensors. The at least one sensor can include at least one of an ECG sensor, an SpO2 sensor, a heart rate sensor, a temperature sensor and a combination thereof. In at least one embodiment, the at least one sensor can include an ECG sensor and an SpO2 sensor, and wherein the system is configured to calculate respiratory rate based on signals from the ECG sensor and the SpO2 sensor. The at least one sensor can include an infrared or other temperature sensor.

In at least one embodiment, the system can include or have access to a database comprising animal data and the animal data can be or include data representing normal vitals or vitals ranges for one or more animals. The data representing normal vitals for one or more animals can include data based on at least one of age, breed, sex, species and a combination thereof. The data representing normal vitals for one or more animals can include at least one of a minimum value and a maximum value, which values can be derived automatically based on existing data or, as another example, can be input by a user. A system can include one or more interfaces, such as graphical or other interfaces, that enables a user to input data or other information into the system, such as acceptable or unacceptable vital sign information pertaining to one or more patients.

In at least one embodiment, a system can include or have access to a server configured to receive patient data and at least one computer program housed within or accessible by the server. The at least one computer program can be configured to analyze patient data, analyze data representing normal or abnormal vitals for one or more animals, and determine whether the patient data is within a normal or abnormal range. The at least one computer program can be configured to display animal vital sign information to one or more users, such as on dedicated or multiuse devices having displays. One or more ranges of normal vitals can include minimum and maximum values for at least one of ECG, SpO2, heart rate, temperature and a combination thereof. Patient data can include data representing at least one of age, breed, sex, species and a combination thereof.

In at least one embodiment, a system can include one or more graphical user interfaces configured to prompt a user to input electronic patient data, the electronic patient data comprising at least one of age, breed, sex, species, a minimum value, a maximum value, and a combination thereof. In at least one embodiment, a system can include one or more graphical user interfaces and at least one computer program configured to cause at least one alarm at the graphical user interface(s) based on the determination of whether patient data is within a normal or otherwise acceptable range. An at least one alarm can include at least one of a visual alarm, an audible alarm, a mechanical alarm and a combination thereof.

In at least one embodiment, a system can include at least one computer program configured to execute one or more algorithms based on one or more inputs derived from patient data and to identify at least one range of normal vitals. A system can include a graphical user interface in data communication with a controller and the graphical user interface can be configured to display information regarding at least one of ECG, SpO2, heart rate, temperature and respiratory rate based on input from at least one sensor coupled to a sensor module. A sensor module can be disposed in sensing communication with a patient. A system can include a plurality of sensor modules and can be adapted for monitoring one or more vital signs of each of a plurality of patients, simultaneously or otherwise.

In at least one embodiment, a system can include at least one controller configured to transmit data from one or more sensors to a server and at least one computer program housed within or accessible by the server can be configured to store, in a database, historical data that represents a series of vital sign readings for at least one patient. A system can include at least one of a visual indicator, an audible indicator and a mechanical indicator attached to a housing and electrically coupled to a controller. A system can be configured to provide a user with at least one of a visual indication, an audible indication and a mechanical indication in response to the presence or absence of one or more conditions based on input from at least one sensor. A system can provide one or more indicators or alarms at a sensor module and/or at a remote user device, simultaneously, selectively, or otherwise.

In at least one embodiment, a system can include a server configured to receive data, at least one computer program housed within or accessible by the server, and a graphical user interface in wireless communication with the server. The controller can be configured to transmit data regarding one or more vital signs of one or more patients to a server. At least one computer program can be configured to display data regarding at least one vital sign on one or more graphical user interfaces. In at least one embodiment, a sensor module can include three or more of an ECG sensor, an SpO2 sensor, a heart rate sensor and a temperature sensor and a system can be configured to sense at least three vital signs simultaneously. In at least one embodiment, a sensor module can include two or more of an ECG sensor, an SpO2 sensor, a heart rate sensor and a temperature sensor and a system can be configured to sense at least two vital signs simultaneously.

BRIEF DESCRIPTION OF THE SEVERAL VIEWS OF THE DRAWINGS

FIG. 7 is one of many embodiments of a dashboard GUI according to the disclosure.

FIG. 8 is another of many embodiments of a dashboard GUI according to the disclosure.

Figure 10:
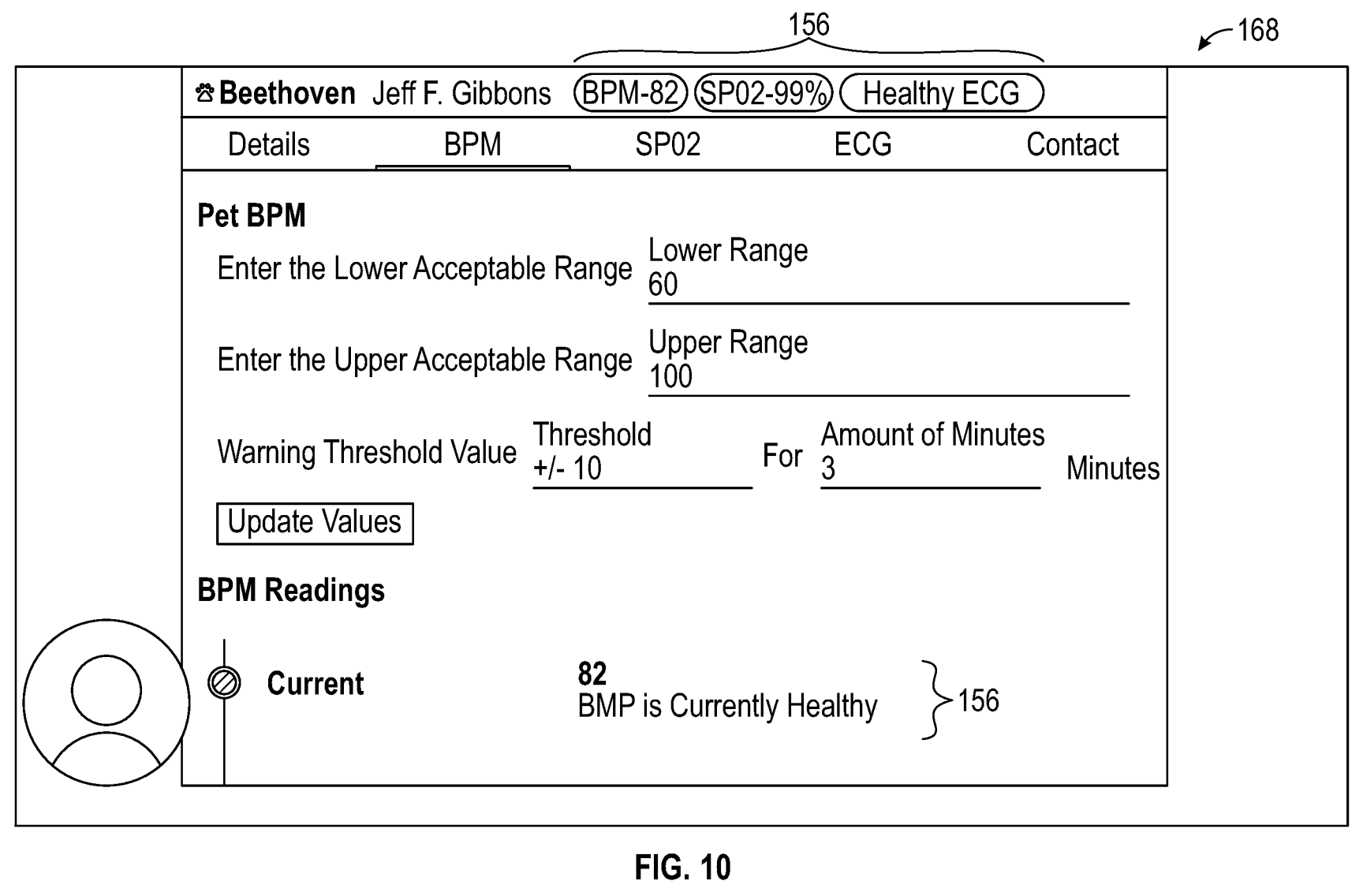

FIG. 10 is one of many embodiments of a BPM GUI according to the disclosure.

FIG. 11 is one of many embodiments of an SpO2 GUI according to the disclosure.

DETAILED DESCRIPTION OF THE INVENTION

Figure 1:
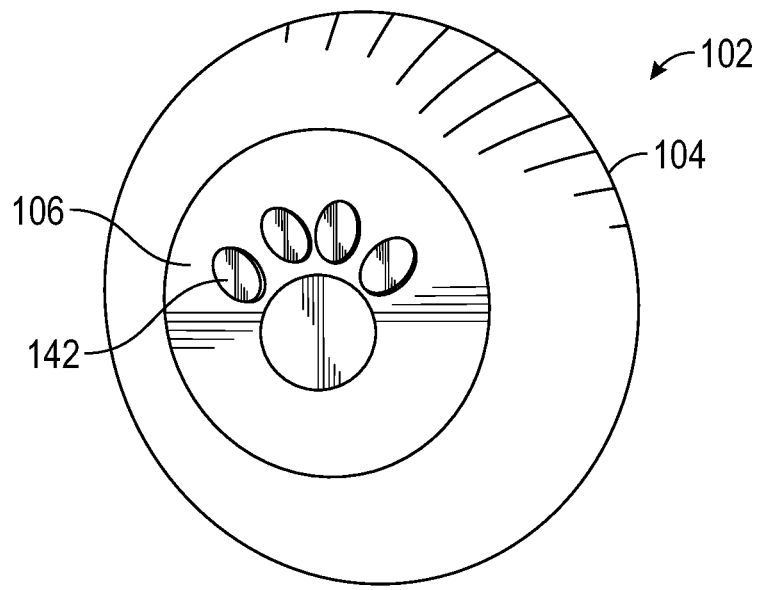
FIG. 1 is a top perspective view of one of many embodiments of a sensor module according to the disclosure.

The Figures described above and the written description of specific structures and functions below are not presented to limit the scope of what Applicants have invented or the scope of the appended claims. Rather, the Figures and written description are provided to teach any person skilled in the art to make and use the inventions for which patent protection is sought. Those skilled in the art will appreciate that not all features of a commercial embodiment of the present disclosure are described or shown for the sake of clarity and understanding. Persons of skill in this art will also appreciate that the development of an actual commercial embodiment incorporating aspects of the present disclosure will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, location and from time to time. While a developer's efforts might be complex and time-consuming in an absolute sense, such efforts would be, nevertheless, a routine undertaking for those of skill in this art having benefit of this disclosure. It must be understood that the embodiments disclosed and taught herein are susceptible to numerous and various modifications and alternative forms. The use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the Figures and are not intended to limit the scope of the disclosure. The terms "including" and "such as" are illustrative and not limitative. The terms "couple," "coupled," "coupling," "coupler," and like terms are used broadly herein and can include any method or device for securing, binding, bonding, fastening, attaching, joining, inserting therein, forming thereon or therein, communicating, or otherwise associating, for example, mechanically, magnetically, electrically, chemically, operably, directly or indirectly with intermediate elements, one or more pieces of members together and can further include without limitation integrally forming one functional member with another in a unity fashion. The coupling can occur in any direction, including rotationally. Unless otherwise indicated, the words "and" and "or" mean "and/or" and the word "can" means "can but need not."

Applicants have created devices, systems and methods for monitoring vitals, such as canine vitals, and alerting veterinary personnel or other users to a condition(s) or potential condition(s) of one or more patients being monitored. While embodiments of the disclosure are described herein with reference to canines for illustrative purposes, one or more of the systems and methods of the present disclosure are not so limited and can alternatively, or collectively, be used for other animals, which can be or include any animal or animals (including humans).

Figure 2:
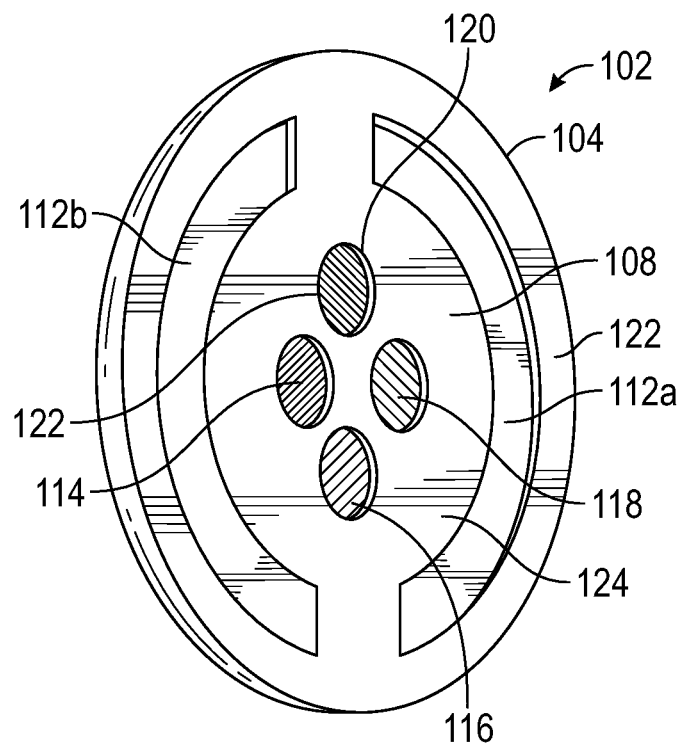
FIG. 2 is a bottom perspective view of the sensor module of FIG. 1.
Figure 3:
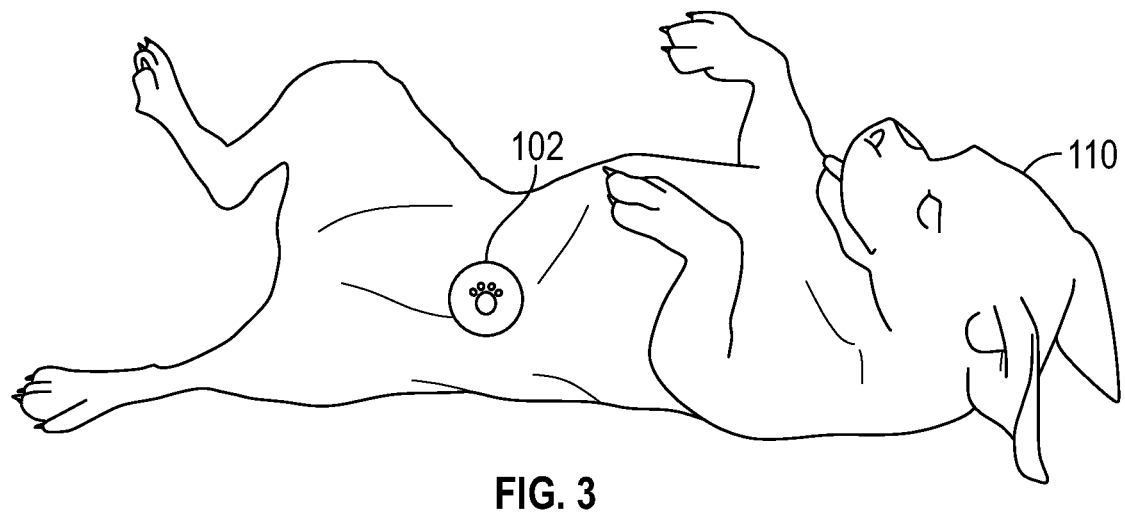
FIG. 3 is a schematic view of the sensor module of FIG. 1 coupled to an animal.
Figure 4:
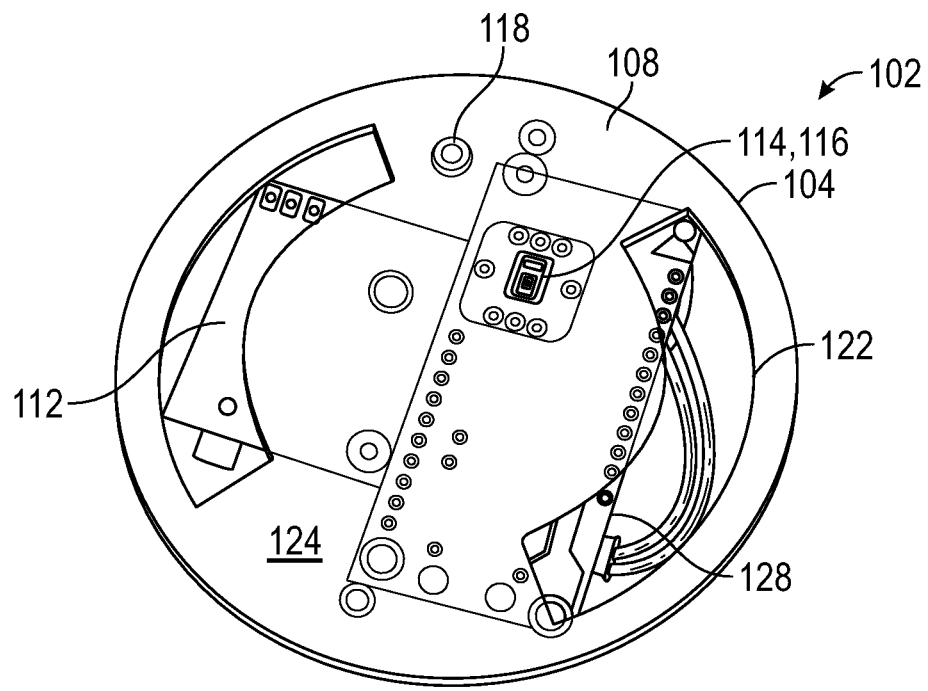
FIG. 4 is a bottom view of the sensor module of FIG. 1 with the ECG plates removed.
Figure 5:
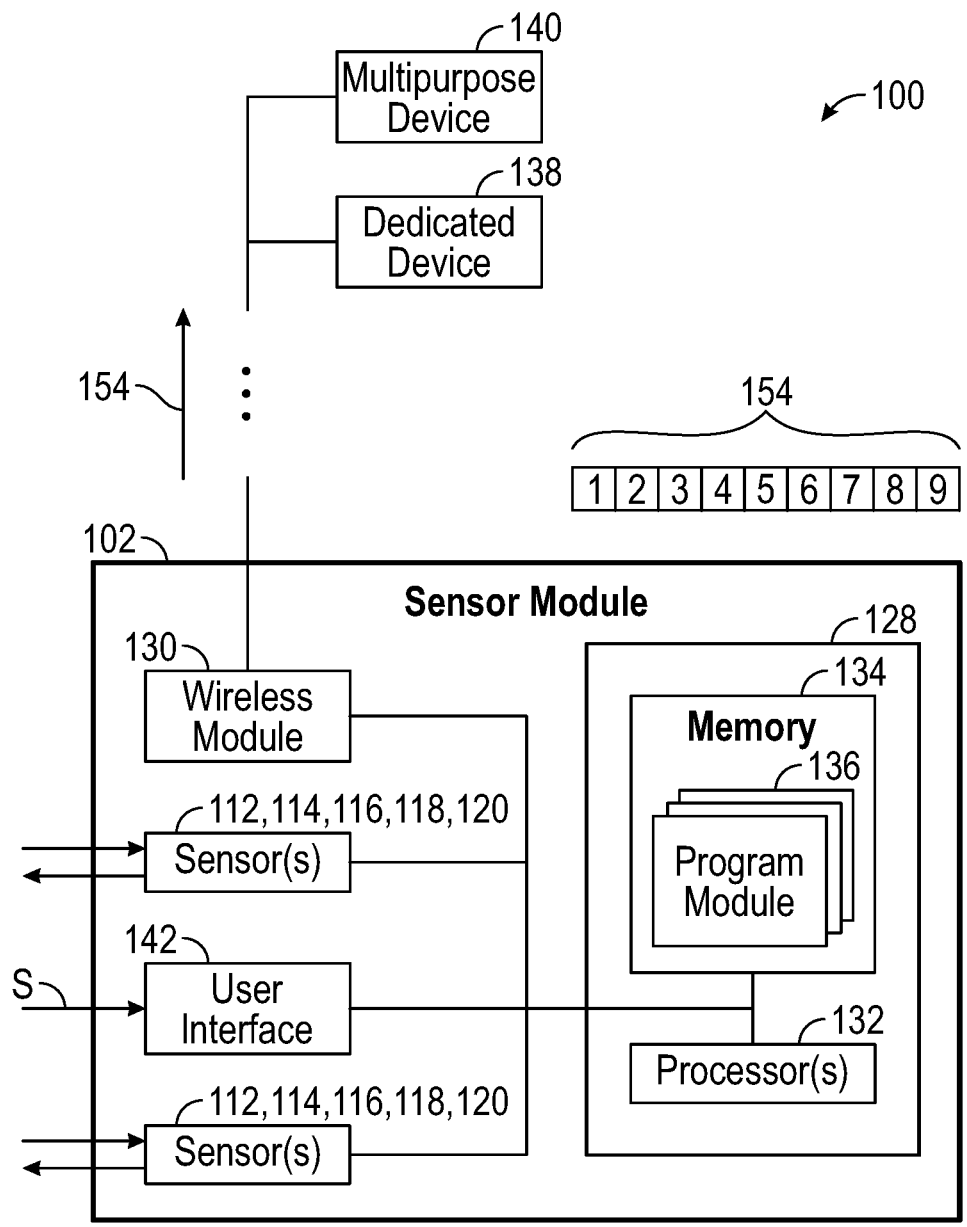
FIG. 5 is a schematic view of one of many embodiments of a monitoring system according to the disclosure and illustrating aspects of a sensor module in communication with display modules.
Figure 6:
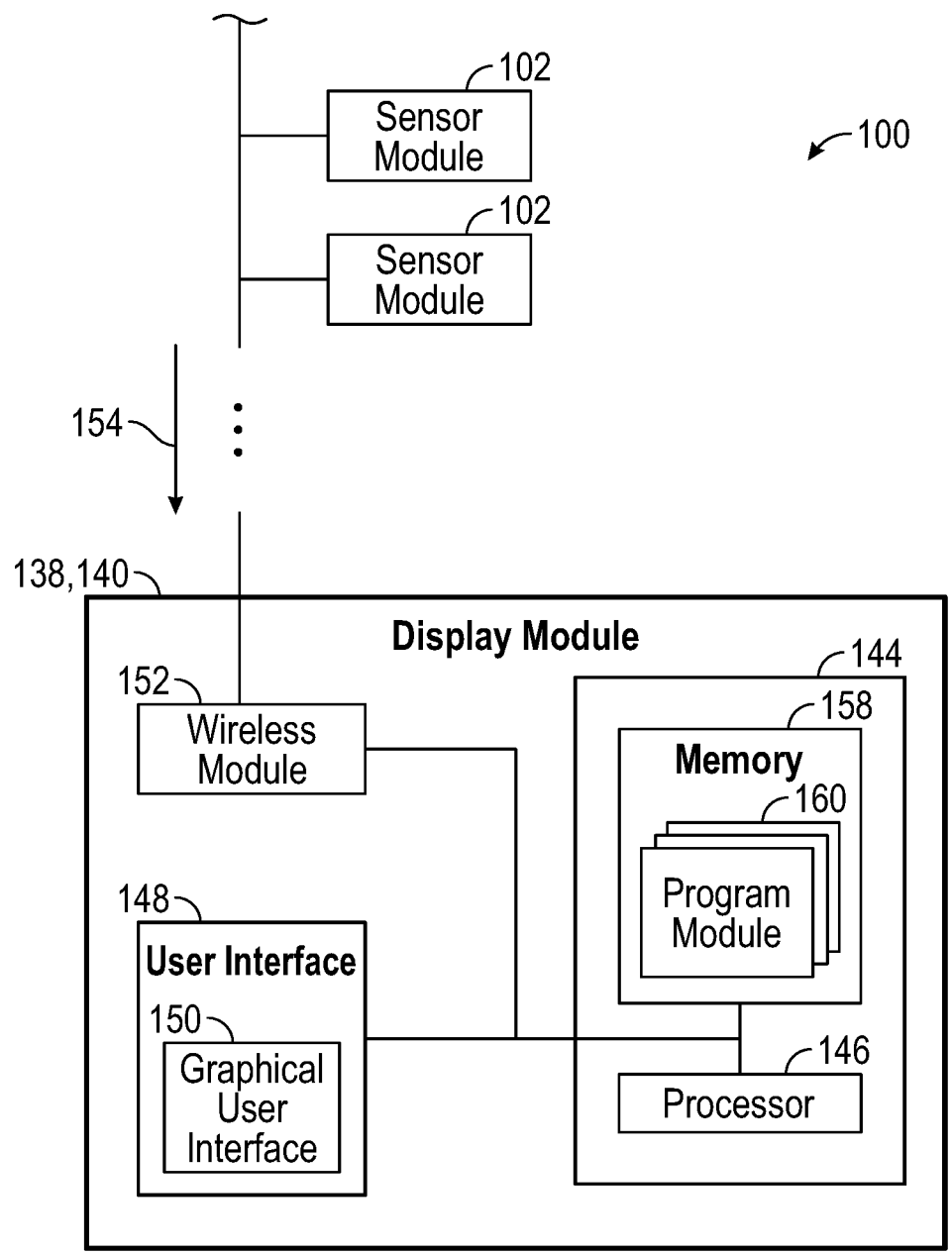
FIG. 6 is another schematic view one of many embodiments of a monitoring system according to the disclosure and illustrating aspects of a display module in communication with a sensor module.
Figure 9:
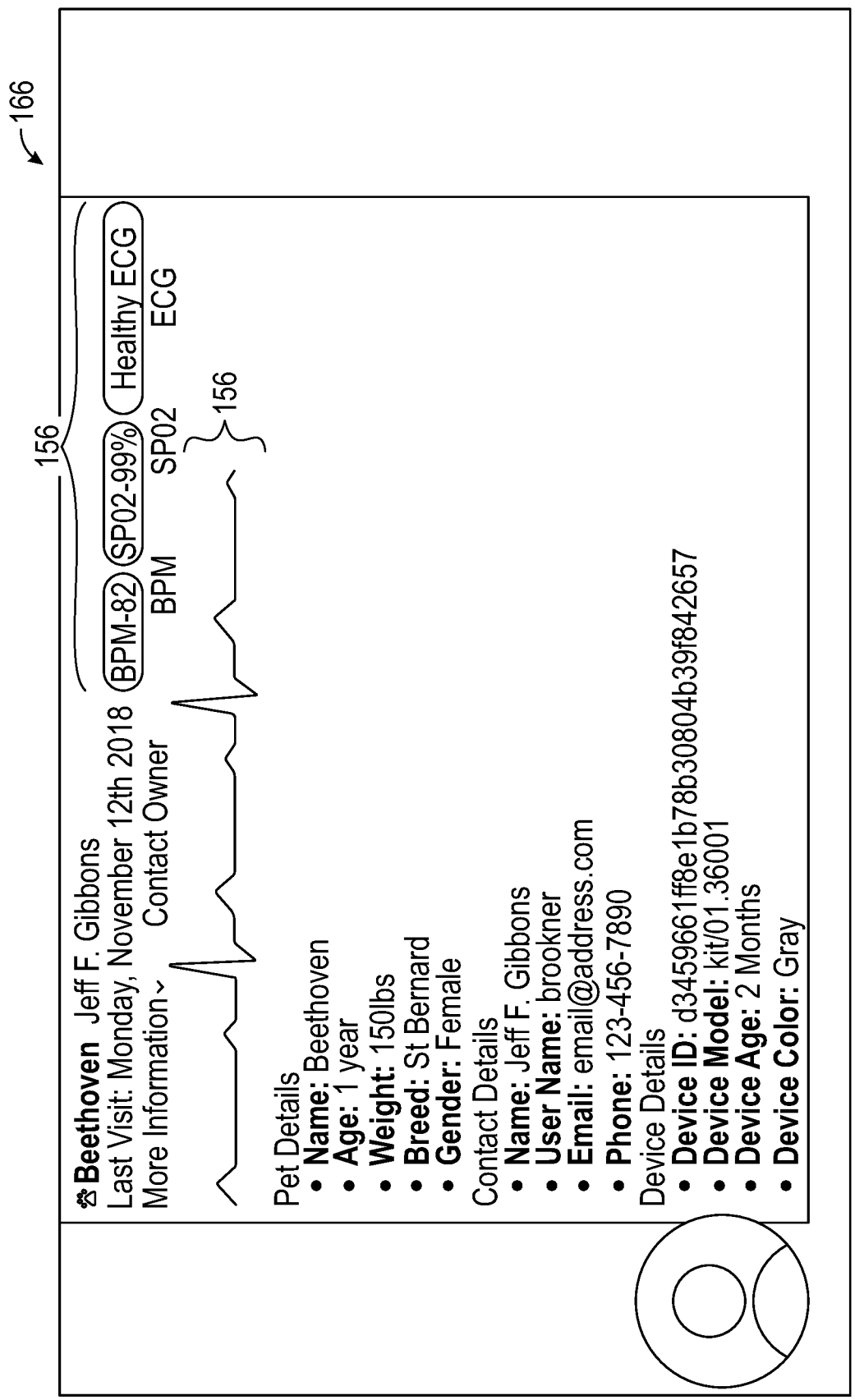
FIG. 9 is one of many embodiments of a patient GUI according to the disclosure.
Figure 13:
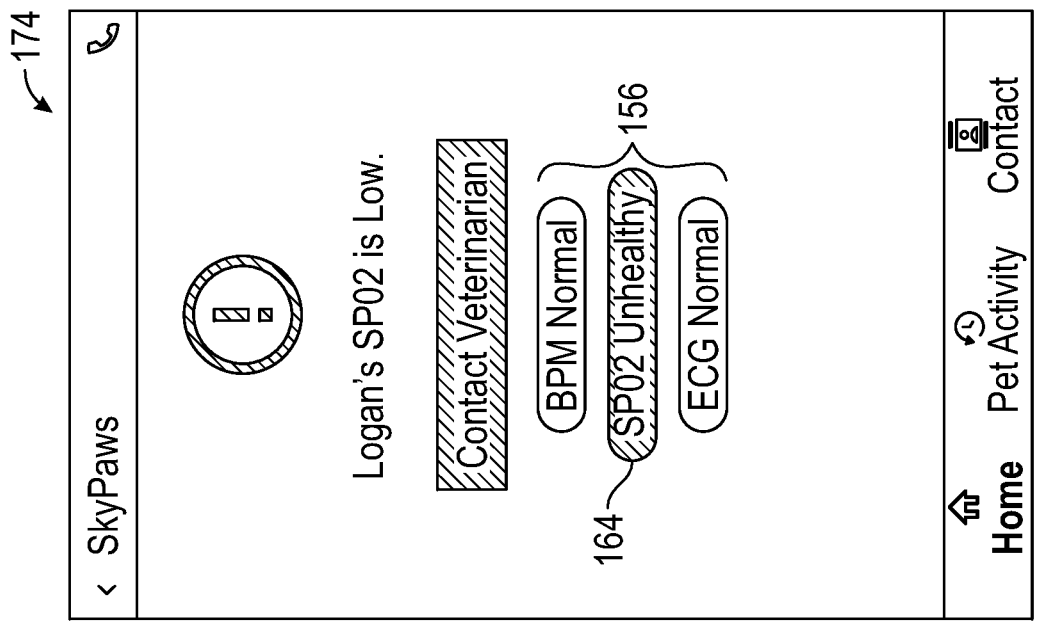
FIG. 13 is another of many embodiments of a summary GUI according to the disclosure.
Figure 12:
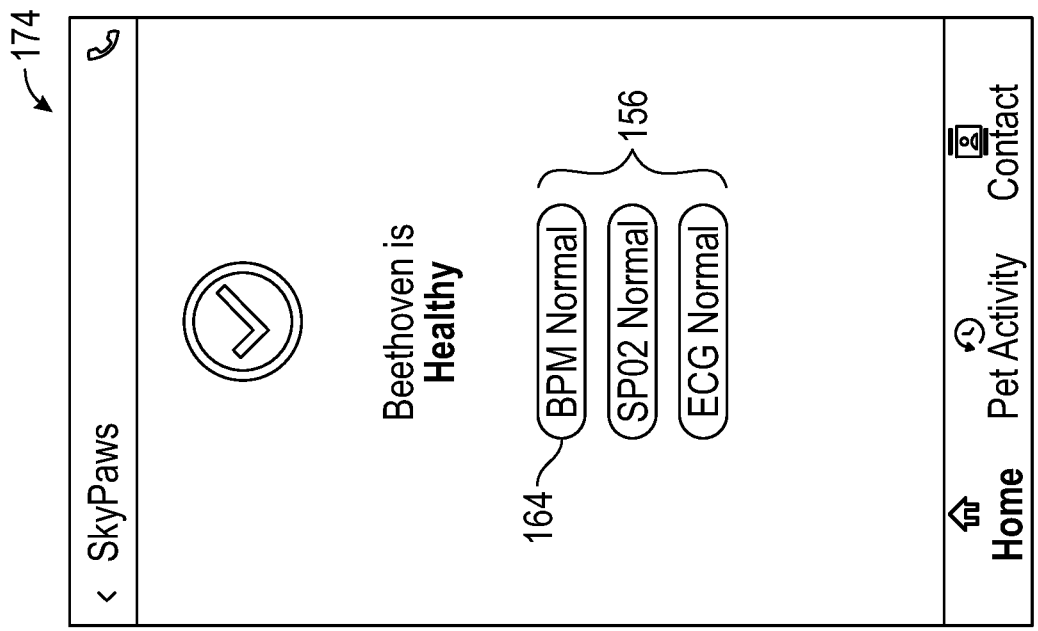
FIG. 12 is one of many embodiments of a summary GUI according to the disclosure.
Figure 14:
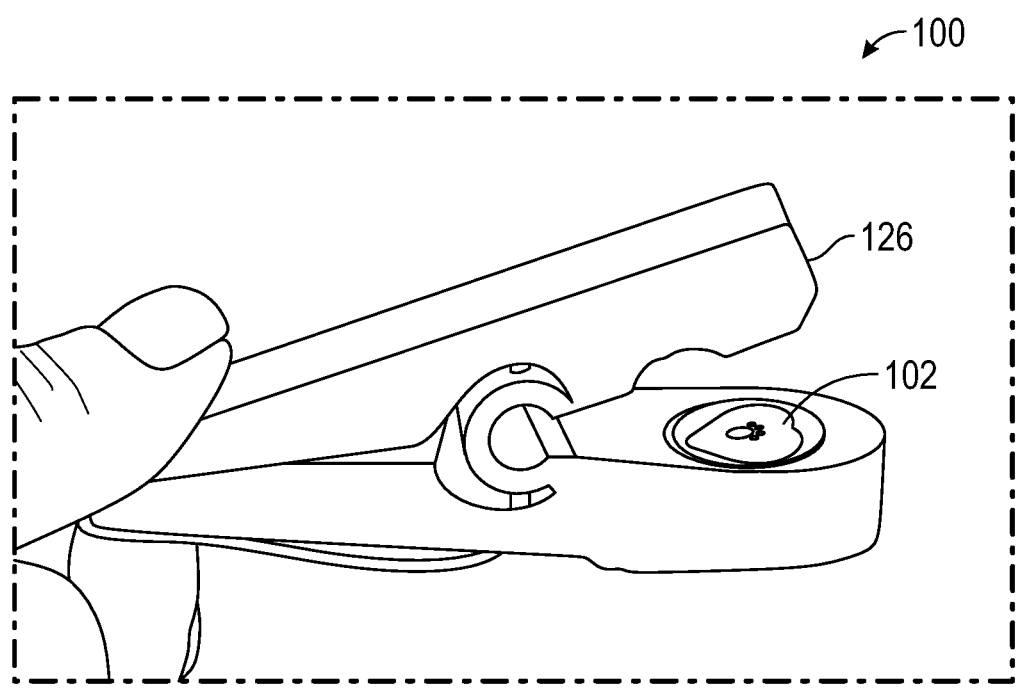
FIG. 14 is one of many embodiments of a sensor module coupled to a paw clip according to the disclosure.

FIG. 1 is a top perspective view of one of many embodiments of a sensor module according to the disclosure. FIG. 2 is a bottom perspective view of the sensor module of FIG. 1. FIG. 3 is a schematic view of the sensor module of FIG. 1 coupled to an animal. FIG. 4 is a bottom view of the sensor module of FIG. 1 with the ECG plates removed. FIG. 5 is a schematic view of one of many embodiments of a monitoring system according to the disclosure and illustrating aspects of a sensor module in communication with display modules. FIG. 6 is another schematic view one of many embodiments of a monitoring system according to the disclosure and illustrating aspects of a display module in communication with a sensor module. FIG. 7 is one of many embodiments of a dashboard GUI according to the disclosure. FIG. 8 is another of many embodiments of a dashboard GUI according to the disclosure. FIG. 9 is one of many embodiments of a patient GUI according to the disclosure. FIG. 10 is one of many embodiments of a BPM GUI according to the disclosure. FIG. 11 is one of many embodiments of an SpO2 GUI according to the disclosure. FIG. 12 is one of many embodiments of a summary GUI according to the disclosure. FIG. 13 is another of many embodiments of a summary GUI according to the disclosure. FIG. 14 is one of many embodiments of a sensor module coupled to a paw clip according to the disclosure. FIGS. 1-14 will be described in conjunction with one another.

In at least one embodiment, a system 100 for monitoring one or more animal vital signs (or "vitals") according to the disclosure can include a sensor module 102 for being coupled to or otherwise disposed in sensing communication with an animal's body. Sensor module 102 can include a housing 104 for at least partially enclosing, holding or otherwise supporting one or more other system components. Sensor module 102 can have one or more sides, which can include a first side 106, such as a top or other side, and a second side 108, such as a bottom or other side. One or more sides, such as second side 108, can be configured to be disposed toward an animal 110, such as a dog (see, e.g., FIG. 3), which can include being disposed in at least partial contact therewith (including, but not limited to full contact). As shown in the exemplary embodiment of FIGS. 1-3, which is but one of many, sensor module 102 can, in at least one embodiment, be at least generally disk shaped or dome shaped, such as a puck shape or truncated semispherical shape. However, this need not be the case and sensor module 102 can be or include any shape according to an implementation of the disclosure. One or more sides can but need not be at least partially flat.

Housing 104 can be made at least partially of plastic or any other material according to an implementation of the disclosure. Housing 104 can be or can include a unitary body or, as another example, can include a plurality of housing portions coupled to one another, such as a base and a cover removably or permanently coupled to one another for holding or supporting one or more other components of sensor module 102 therein or thereon. Two or more portions of housing 104 can be coupled to one another in any manner according to an implementation of the disclosure, such as by friction fit, interference fit, threads, one or more mechanical fasteners (e.g., screws), adhesives, epoxy or otherwise, separately or in combination, in whole or in part. Housing 104 can be any size and shape according to an implementation of the disclosure and can preferably be sized and shaped to hold or otherwise support one or more of the other components of sensor module 102 further described below and for being conveniently and comfortably coupled with an animal. In at least one embodiment, which is but one of many, housing 104 can have a diameter or other major dimension of about 3 inches or, as other examples, in the range of 1 to 5 inches. Housing 104 can have a thickness or height of about ¾ inch, or more or less. The shape and size of housing 104 can vary from one embodiment to another and can depend, for example, on factors such as the number of sensors present in a given embodiment or the sizes of the components disposed in housing 104, such as one or more of the components discussed in further detail below.

In at least one embodiment, second side 108 can be adapted for being disposed in sensing communication with an animal's body in one or more locations. For example, in at least one embodiment, sensor module 102 can be adapted for contact with an animal's rib cage as shown for illustrative purposes in FIG. 3. For instance, sensor module 102 can be adapted for placement in one or more locations along the lateral aspect of the ribs, such as midway or otherwise between the dorsum and ventrum. However, this need not be the case and, in at least one embodiment, sensor module 102 can be disposed on any of one or more other areas of a patient's body, such as on the neck, chest, back, upper leg, lower leg, foot, head or another location. Placement of sensor module 102 on or near an animal's rib cage can be advantageous in at least some embodiments, such as by way of facilitating sensing of two or more vitals simultaneously, which can include all monitored vitals according to an implementation of the disclosure. However, one or more other body placements are feasible as well, even if such a placement may restrict or limit the ability of an embodiment of sensor module 102 to sense one or more vitals. In general, sensor module 102 can be placed anywhere on an animal's body as needed or desired for an implementation of the disclosure and such placement can depend on which vital or vitals a user wishes to monitor at the moment.

Similarly, sensor module 102 can be coupled to or otherwise disposed in sensing communication with a patient's body in any manner or manners according to an implementation of the disclosure. For example, sensor module 102 can be attached to a patient with tape, such as hair-safe tape, medical tape, or another type of tape. As another example, sensor module 102 can be attached to a patient with a harness, such as an elastic or inelastic band, strap or other lashing, for holding sensor module 102 in one or more positions relative to a patient's body. As yet another example, in at least one embodiment, sensor module 102 can be coupled to a clip 126, such as a paw clip, for holding sensor module 102 in sensing communication with the webbing or another portion of an animal's paw.

Sensor module 102 can include one or more sensors for sensing one or more vital signs of an animal, such as for monitoring the state of one or more of a patient's essential body functions. Such vital signs include things like pulse rate, temperature, respiration rate, blood pressure, heart activity and blood oxygen level. In at least one embodiment, sensor module 102 can include one or more electrocardiogram (ECG or EKG) sensors 112 for measuring electrical activity of the heart or heartbeat. In at least one embodiment, ECG sensor 112 can include two or more plates 112a, 112b, such as electrodes or other conductors, for electrically communicating with one another to measure or monitor heart activity. One example of a suitable ECG sensor 112 that can be utilized in one or more embodiments of the disclosure is the Protocentral Max30003 single-lead ECG breakout board (e.g., v2) available from Protocentral. In at least one embodiment, sensor module 102 can include one or more peripheral capillary oxygen saturation (SpO2) sensors 114 for sensing or estimating an amount of oxygen in the blood. One example of a suitable SpO2 sensor 114 that can be utilized in one or more embodiments of the disclosure is the MAXREFDES117# heart-rate and pulse oximetry monitor available from Maxim Integrated. In at least one embodiment, sensor module 102 can include one or more pulse or heart rate sensors 116 for sensing a patient's heart rate. One example of a suitable heart rate sensor 116 that can be utilized in one or more embodiments of the disclosure is the MAXREFDES117# heart-rate and pulse oximetry monitor available from Maxim Integrated. In at least one embodiment, sensor module 102 can include one or more thermometers or temperature sensors 118 for sensing a patient's body temperature. One example of a suitable temperature sensor 118 that can be utilized in one or more embodiments of the disclosure is the ZTP-1155-ND analog -20C-100C TO205AA sensor available from Digi-Key. The presently commercially available sensors mentioned above are but some examples of many that can be utilized for at least one embodiment of sensor module 102 and are identified herein for purposes of illustration and not limitation. In at least one embodiment, sensors 112, 114, 116, 118, 120 can be or include any sensor(s) required or desired for an implementation of the disclosure, whether now known or future developed.

In at least one embodiment, sensor module 102 can include one or more respiratory rate sensors 120 for sensing a patient's breathing rate, such as by measuring respiratory impedance, or the change in distance from the sensor when the patient is inspiring (breathing in) versus expiring (breathing out). For example, sensor module 102 or respiratory rate sensor 120 can be disposed on or otherwise relative to a patient's rib cage for picking up breathing motion. In at least one embodiment, it can be advantageous to dispose respiratory rate sensor 120 in sensing communication with the widest portion of a patient's rib cage, as a relatively larger change in dimension can occur there during breathing which can allow for easier or more accurate respiratory rate measurement, e.g., because it can be easier for respiratory rate sensor 120 to sense relatively larger differences in dimension. However, this need not be the case and respiratory rate sensor 120 can be positioned anywhere on a patient's body according to an implementation of the disclosure, which positioning can depend in part on the particular type of respiratory rate sensor 120 utilized for such an implementation of sensor module 102.

Sensor module 102 can include any one or more of the aforementioned sensors required or desired for an implementation of the disclosure. In at least one embodiment, sensor module 102 can advantageously include all of the aforementioned sensors 112, 114, 116, 118, 120. In at least one embodiment, one or more sensors 112, 114, 116, 118, 120 can be absent, which can, but need not, preclude the ability of sensor module 102 or system 100 to determine or estimate a corresponding vital sign. For instance, in at least one embodiment, sensor module 102 can include one or more of sensors 112, 114, 116, 118 and respiratory rate sensor 120 can be absent. In such an embodiment, which is but one of many, sensor module 102 or system 100 can nonetheless be adapted for monitoring a patient's respiratory rate. More specifically, sensor module 102 or system 100 can be adapted for calculating a patient's respiratory rate based on sensed information from ECG sensor 112 and SpO2 sensor 114. Any of sensors 112, 114, 116, 118, 120 can be positioned or arranged in any manner or order on, in or otherwise relative to housing 104 or a portion thereof for operation in accordance with aspects of the disclosure or an implementation thereof. The various sensor positions illustrated in the Figures are illustrative only and are presented for purposes of explanation and example.

One or more of sensors 112, 114, 116, 118, 120 can be disposed at least partially within housing 104 and operably arranged relative to second side 108 for sensing communication with a patient's body when sensor module 102 is coupled to or otherwise disposed in sensing relation to a patient. One or more of sensors 112, 114, 116, 118, 120 or one or more portions thereof can at least partially extend or protrude into or through second side 108 as needed or desired for a sensor type according to an implementation of the disclosure. For instance, in at least one embodiment, sensor module 102 can include one or more apertures 122, such as holes, windows or other openings, for coupling with one or more of sensors 112, 114, 116, 118, 120 or otherwise supporting sensing communication between one or more of sensors 112, 114, 116, 118, 120 and a patient's body. Any of sensors 112, 114, 116, 118, 120 (or applicable portions thereof) can be recessed relative to, extend from or be flush with outside surface 124 of second side 108, as needed or desired. For example, in at least one embodiment, plates 112a, 112b of ECG sensor 112 can be disposed at least partially in or through second side 108 for contacting a patient's skin during use. In at least one embodiment, one or more of sensors 112, 114, 116, 118, 120 can be adapted to sense through second side 108 or a portion thereof (which can, but need not, be at least partially transparent depending on, e.g., a sensor type at hand).

Sensor module 102 can include one or more controllers 128 disposed within or otherwise coupled to housing 104 for controlling or supporting control of one or more aspects of sensor module 102 or a system 100 comprising one or more sensor modules 102. Controller 128 can be operatively coupled to one or more of sensors 112, 114, 116, 118, 120, such as by way of one or more switch devices or otherwise, for controlling one or more aspects of operation. Sensor module 102 can include one or more wireless modules 130 disposed within or otherwise coupled to housing 104 for communicating with one or more other components of system 100. The controller can include a processor. The processor can be communicative with one or more sensors and/or the wireless module through an interface. Sensor module 102 can include a non-transitory machine-readable memory connected to the controller. The memory can have instructions recorded thereon that, when read by the processor, cause the processor to undertake one or more actions.

In at least one embodiment, controller 128 can include a processor 132 and a memory 134. Memory 134 can be or include a non-transitory machine-readable medium having one or more program modules 136 recorded thereon containing instructions that, when read by processor 132, cause controller 128 to execute one or more operations. The instructions can cause sensor module 102 to acquire data 154 indicative of one or more patient vital signs according to signals from one or more of sensors 112, 114, 116, 118, 120. In at least one embodiment, the instructions can cause sensor module 102 to compress the data. In at least one embodiment, the instructions can cause sensor module 102 to provide data 154 wirelessly (and/or via wire, if desired) to one or more display modules, which can include one or more dedicated devices 138 and/or one or more multipurpose devices 140, which can include one or more computers, smart phones, tablets or other electronic devices. Sensor module 102 can include one or more power sources (not shown), such as a battery, disposed in or otherwise coupled to housing 104 for providing power to one or more components of sensor module 102. In at least one embodiment, sensor module 102 can include a power button 142 accessible from outside housing 104 for turning the unit on or off as desired. In at least one embodiment, sensor module 102 can include one or more other buttons or user interfaces (not shown) accessible from outside housing 104 for controlling one or more other aspects of sensor module 102 (e.g., activating or deactivating one or more sensors, initiating syncing among sensor module 102 and one or more display modules 138, 140, etc.). In at least one embodiment, a multipurpose device 140 can be a mobile device, e.g., a mobile telephone, with a user interface 148 arranged to display one or more graphical user interfaces (further described below) graphically presenting information regarding one or more monitored vital signs. In at least one embodiment, multipurpose device 140 can be a mobile telephone having recorded thereon an application which receives data 154 and determines one or more vital sign readings 156 based on data 154 using on-board computing resources of the mobile device. As will be appreciated by those of skill in the art having the benefits of the present disclosure, utilizing on-board computing resources remote from sensor module 102 can prolong the expected life of one or more batteries used to provide power to sensor module 102.

In at least one embodiment, a display module 138, 140 can include a controller 144 and a processor 146, a user interface 148 with a graphical user interface (GUI) 150, and a wireless module 152. Controller 144 can be operatively connected to wireless module 152 and user interface 148 and can be configured to receive data 154 from sensor module 102 via wireless module 152. Controller 144 can be configured to recognize sensor module 102, such as upon receipt of data including synchronization indicator S (see FIG. 5), controller 144 thereafter or otherwise recognizing data 154 received from one or more sensor modules 102 and determining one or more vital signs or vital sign readings 156 (see, e.g., FIGS. 7-8) using data 154 from sensor module 102 based on readings from one or more of sensors 112, 114, 116, 118, 120, which can be or include any of such sensors according to an implementation of the disclosure. Controller 144 can include a memory 158. Memory 158 can be or include a non-transitory machine-readable medium with one or more program modules 160 having instructions recorded thereon that, when read by processor 146, cause controller 144 to execute one or more operations. The instructions can cause controller 144 to convert sensor data 154 into human readable information (if need be) and to display such information on one or more display modules 138, 140. In particular, the instructions can cause controller 144 to calculate at least one of heart rate (e.g., in beats per minute (BPM)), temperature (e.g., in degrees Fahrenheit or degrees Celsius), respiration rate (e.g., in breaths per minute), heart activity (e.g., in volts or millivolts versus time) and blood oxygen level (e.g., as a percentage hemoglobin in the blood that is saturated with oxygen) and to provide indication of one or more of such determinations to a user interface, e.g., user interface 148 remote from sensor module 102. Such calculations and indication can be provided on a per sensor module 102 or per patient basis for any number of sensor modules 102 incorporated into an implementation of system 100.

In at least one embodiment, system 100 can include one or more GUIs for supporting one or more aspects of system operation, such as via one or more display modules 138, 140. For example, system 100 can include a dashboard GUI 162 for displaying information regarding one or more patients, which can be or include vital sign readings 156 corresponding to any of one or more of sensors 112, 114, 116, 118, 120. System 100 can include one or more visual indicators 164 for indicating a state of one or more vital signs, such as a visual indicator 164 for each of one or more vital sign readings 156 that is displayed in one color (e.g., green) when a reading is normal and another color (e.g., red) when a reading is abnormal. System 100 can also include one or more audible, physical, mechanical or other indicators or alarms (not shown) for indicating to a user that one or more patients needs assistance or has a vital sign that may be abnormal or approaching abnormal. For example, in at least one embodiment, system 100 can be adapted for sounding an alarm via one or more speakers associated with or incorporated into one or more display modules 138, 140. Similarly, system 100 can be adapted for causing a display module 138, 140 to vibrate upon the occurrence or absence of a vital sign event, such as by way of the vibration function common in many smartphones. In at least one embodiment, dashboard GUI 162 can include various patient information, such as pet name, owner name, date information, contact information, historical information (e.g., date of most recent visit), and other information, which can be or include any information desired for an implementation of the disclosure (see, e.g., FIG. 7). In at least one embodiment, dashboard GUI 162 can include search functions, sort functions, display options and the like (see, e.g., FIG. 8).

In at least one embodiment, system 100 can include one or more patient GUIs 166 for displaying additional details pertaining to a patient (see FIG. 9). For example, patient GUI 166 can include one or more vital sign readings 156 corresponding to any of one or more of sensors 112, 114, 116, 118, 120. As another example, patient GUI 166 can include patient information such as name, age, weight, breed, gender, contact information and the like. In at least one embodiment, patient GUI 166 can include one or more details pertaining to a particular sensor module 102 utilized for a given patient, such as a device identification number, device model number, the age of a device, the color of the device, remaining battery life of the device, etc.

In at least one embodiment, system 100 can include one or more vital sign GUIs for displaying additional details pertaining to a particular vital sign or vital sign reading 156 for a patient (see, e.g., FIGS. 10-11). For example, a vital sign GUI can be or include a BPM GUI 168 for displaying and/or receiving information pertaining to a patient's heart rate, such as current or historical heart rate readings and information pertaining to the timing of such readings. As another example, in at least one embodiment, BPM GUI 168 can allow a user to input information into system 100 such as parameters relating to treatment or monitoring of one or more patients. For instance, a user can input parameters such as high and low values for an acceptable heart rate and system 100 can be adapted to provide an indication or alarm to the user in the event a patient's heart rate deviates or may deviate from such an acceptable range or value. BPM GUI 168 can allow a user to enter a warning threshold value or value range, which can but need not be dependent on time, and system 100 can be adapted to provide an indication or alarm to the user in the event a patient's heart rate falls within the threshold and/or remains within the threshold for a user determined (or other) period of time.

As another example, a vital sign GUI can be or include an SpO2 GUI 170 (see FIG. 11) for displaying and/or receiving information pertaining to a patient's SpO2, such as current or historical SpO2 readings and information pertaining to the timing of such readings. SpO2 GUI 170 can likewise allow a user to input information into system 100 such as parameters relating to treatment or monitoring of one or more patients. For instance, a user can input parameters such as high and low values for an acceptable SpO2 range and system 100 can be adapted to provide an indication or alarm 172 to the user in the event a patient's SpO2 deviates or may deviate from such an acceptable range or value. System 100 can include one or more similar vital sign GUIs for one or more other vital signs, which can be any vital sign monitored by one or more sensor modules 102. As yet another example, system 100 can include one or more summary GUIs 174 (see FIGS. 12-13) for summarizing (or detailing, if desired) information relating to the monitoring of one or more patients. For instance, a summary GUI 174 can provide an indication of whether a patient is generally healthy and/or of whether one or more vital signs are generally within a healthy or normal range or state. Summary GUI 174 can in at least some embodiments provide other information or functionality, such as the ability to contact a doctor or owner, historical or other pet activity information, contact information for one or more persons, etc. Summary GUI 174 can in at least some embodiments include one or more visual indicators 164 corresponding to one or more vital signs, which can be or include any vital sign(s) according to an implementation of the disclosure. In at least one embodiment, one or more summary GUIs 174 and/or any of the GUIs described herein can be embodied in a smartphone application or "app" that runs on one or more display modules 138, 140, such as a smartphone or other multipurpose device 140 utilized by, e.g., medical personnel or a pet owner.

In at least one embodiment, system 100 can allow a user to selectively choose which of sensors 112, 114, 116, 118, 120 are operable and/or which of vital sign readings 156 are active or displayed at any given time, such as via one or more of the GUIs described above or another GUI that incorporates such functionality. In other words, in at least one embodiment, sensor module 102 can include any two or more sensors and a user may nonetheless wish to utilize/monitor fewer than all available sensors/vital sign readings at any given time. Accordingly, system 100 can be arranged and configured for allowing a user to choose, via a GUI, which of one or more sensors or readings is or are active or inactive at any given time. In at least one embodiment, such a choice can result in the activation or deactivation of one or more sensors. In at least one embodiment, such a choice can result in the activation or deactivation of one or more displays or portions of a display.

As will be appreciated by those skilled in the art having the benefits of the present disclosure, aspects of one or more embodiments of the disclosure can be embodied as a system, method or computer program product. Accordingly, aspects of the present embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more non-transitory computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples of such computer readable storage media include but are not limited to the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on a user's computer, partly on a user's computer, as a stand-alone software package, partly on a user's computer and partly on a remote computer or entirely on a remote computer or server. In the latter scenario, the remote computer may be connected to a user's computer through any type of network, including a local area network (LAN) or a wide area network (WAN), or the connection may be made to an external computer (for example, through the Internet using an Internet Service Provider or via a short-range wireless interconnection such as Bluetooth).

Aspects of the present disclosure can be described with reference to flowchart illustrations and/or block diagrams of methods, apparatuses (devices and systems) and computer program products according to embodiments of the disclosure. Each block of a flowchart illustration and/or block diagram, and combinations of blocks in a flowchart illustration and/or block diagrams, can be implemented by computer program instructions. These computer program instructions may be provided to a processor of a general purpose computer, special purpose computer, or other programmable data processing apparatus to produce a machine, such that the instructions, which executed via one or more processors, create means for implementing the functions/acts specified in the flowchart and/or block diagram block or blocks. The computer program instructions can be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in a flowchart and/or block diagram block or blocks. Each block in a flowchart and/or block diagram can be split into multiple blocks and/or combined with other blocks to make a single block.

In at least one embodiment of system 100, the Arduino Uno and 1Sheeld can be used as controllers, but other controllers and combinations of controllers are possible, including one or more transmitters and receivers. Coding can be done, for example, via Arduino IDE and can be loaded into one or more controllers, which can include memory, from a computer that is connected with a cord or otherwise. Coding can have a variety of formatting orders according to a particular embodiment or implementation of the disclosure. A computer can act as a main power source of a monitoring system, but other power sources are possible, such as a rechargeable battery power source within sensor module 102 and/or a rechargeable battery power source within one or more display modules 138, 140. One or more sensors can be connected to one or more controllers, such as a 1Sheeld via one or more ports. When activated, a sensor can send data to the Arduino Uno or another controller that processes the data and, for example, determines the beats per minute (BPM) or other vital sign reading 156 and/or checks if such reading(s) is/are in tolerable or acceptable ranges, such as for a particular animal/patient. If a reading is not in a tolerable range, then a monitoring system 100 can send one or more signals, which can include a string notification 176, that conveys that a reading is too high or too low. Such information can be sent to the 1Sheeld (or another controller) which can, via Bluetooth, Wi-Fi or otherwise, communicate one or more results to a software application, such as on a computer, smart phone, tablet or other device. The application can display some or all relevant information received, such as by way of a display or GUI described herein, and can do so by one or more modes.

All or part of sensor module 102 or system 100 can be waterproofed and can be powered by a battery, rechargeable battery, or other power source. System 100 can include one or more charging stations (not shown) for charging a battery (not shown) within one or more sensor modules 102, whether separately, simultaneously, wirelessly, via electrodes on sensor module 102, or otherwise. Data from sensor module 102 can be sent to an application on a cellular device or other device. The app can be adapted to update the vitals information for one or more patients in real (or near real) time or other time increments and if an animal becomes or may become tachycardic or go into cardiac arrest (or there is another reason for concern, such as an abnormal vital sign), the system can send a notification, signal or alarm to one or more people logged into the app, such as vet personnel. This can decrease response time so that cardiopulmonary resuscitation (CPR) or other medical care can be performed faster, which can increase chances of survival. A transmitter can be located on, in or apart from housing 104, which can include comprising a second housing or housing unit, such as a housing adapted to couple to a kennel or other structure. However, in at least one advantageous embodiment, such as the exemplary embodiment of FIGS. 1-3, no such second housing or hub is necessary and sensor module 102 can provide a relatively small, convenient, all-in-one package for monitoring one or more vital signs of a patient. One or more housings can include one or more displays, which can display information such as heart rate and oxygen saturation, and can include one or more indicators, such as LEDs or other lights, which can be adapted to indicate one or more conditions or the lack of one or more conditions, such as by blinking, changing colors, patterns, and the like. In at least one embodiment, a monitoring system can include an audible alarm, but need not and can omit an audible alarm, such as for avoiding alarm or distress of one or more animals being monitored or in the vicinity of an animal being monitored. In at least one embodiment, one or more of such indicators and/or alarms can be coupled to and/or housed within housing 104 of sensor module 102.

In at least one embodiment, a monitoring system according to the disclosure can include one or more components housed within or otherwise coupled to one or more paw clips 126, which can include sensors, controllers, receivers, transmitters and other components, separately or in combination, in whole or in part. In at least one embodiment, a monitoring system can include a dog footie (not shown), such as a small bag adapted to be coupled to an animal's foot, which can at least partially support one or more other components of the system.

A system for monitoring animal vitals can include a housing, a controller and one or more sensors for sensing vital signs. The housing can be configured to couple to one or more locations on an animal. A system can be adapted for monitoring two or more vital signs simultaneously and for conveying vital sign information to a user. A system can be adapted for alerting a user to the presence or absence of one or more conditions. A system can include a plurality of sensor units and can be adapted for monitoring a plurality of patients simultaneously.

In at least one embodiment, a system can include a housing having a first side and a second side, a controller disposed within the housing, and at least one sensor operably coupled to the controller and disposed at least partially within the housing, wherein the housing is configured to be coupled to an animal, wherein the second side of the housing is configured to be disposed in direct contact with the animal's skin, wherein the at least one sensor is operably coupled with the second side of the housing, and wherein the at least one sensor is configured to sense at least one vital sign.

In at least one embodiment, the at least one sensor can include a plurality of sensors. The at least one sensor can include at least one of an ECG sensor, an SpO2 sensor, a heart rate sensor, a temperature sensor and a combination thereof. In at least one embodiment, the at least one sensor can include an ECG sensor and an SpO2 sensor, and wherein the system is configured to calculate respiratory rate based on signals from the ECG sensor and the SpO2 sensor. The at least one sensor can include an infrared or other temperature sensor.

In at least one embodiment, the system can include or have access to a database comprising animal data and the animal data can be or include data representing normal vitals or vitals ranges for one or more animals. The data representing normal vitals for one or more animals can include data based on at least one of age, breed, sex, species and a combination thereof. The data representing normal vitals for one or more animals can include at least one of a minimum value and a maximum value, which values can be derived automatically based on existing data or, as another example, can be input by a user. A system can include one or more interfaces, such as graphical or other interfaces, that enables a user to input data or other information into the system, such as acceptable or unacceptable vital sign information pertaining to one or more patients.

In at least one embodiment, a system can include or have access to a server configured to receive patient data and at least one computer program housed within or accessible by the server. The at least one computer program can be configured to analyze patient data, analyze data representing normal or abnormal vitals for one or more animals, and determine whether the patient data is within a normal or abnormal range. The at least one computer program can be configured to display animal vital sign information to one or more users, such as on dedicated or multiuse devices having displays. One or more ranges of normal vitals can include minimum and maximum values for at least one of ECG, SpO2, heart rate, temperature and a combination thereof. Patient data can include data representing at least one of age, breed, sex, species and a combination thereof.

In at least one embodiment, a system can include one or more graphical user interfaces configured to prompt a user to input electronic patient data, the electronic patient data comprising at least one of age, breed, sex, species, a minimum value, a maximum value, and a combination thereof. In at least one embodiment, a system can include one or more graphical user interfaces and at least one computer program configured to cause at least one alarm at the graphical user interface(s) based on the determination of whether patient data is within a normal or otherwise acceptable range. An at least one alarm can include at least one of a visual alarm, an audible alarm, a mechanical alarm and a combination thereof.

In at least one embodiment, a system can include at least one computer program configured to execute one or more algorithms based on one or more inputs derived from patient data and to identify at least one range of normal vitals. A system can include a graphical user interface in data communication with a controller and the graphical user interface can be configured to display information regarding at least one of ECG, SpO2, heart rate, temperature and respiratory rate based on input from at least one sensor coupled to a sensor module. A sensor module can be disposed in sensing communication with a patient. A system can include a plurality of sensor modules and can be adapted for monitoring one or more vital signs of each of a plurality of patients, simultaneously or otherwise.

In at least one embodiment, a system can include at least one controller configured to transmit data from one or more sensors to a server and at least one computer program housed within or accessible by the server can be configured to store, in a database, historical data that represents a series of vital sign readings for at least one patient. A system can include at least one of a visual indicator, an audible indicator and a mechanical indicator attached to a housing and electrically coupled to a controller. A system can be configured to provide a user with at least one of a visual indication, an audible indication and a mechanical indication in response to the presence or absence of one or more conditions based on input from at least one sensor. A system can provide one or more indicators or alarms at a sensor module and/or at a remote user device, simultaneously, selectively, or otherwise.

In at least one embodiment, a system can include a server configured to receive data, at least one computer program housed within or accessible by the server, and a graphical user interface in wireless communication with the server. The controller can be configured to transmit data regarding one or more vital signs of one or more patients to a server. At least one computer program can be configured to display data regarding at least one vital sign on one or more graphical user interfaces. In at least one embodiment, a sensor module can include three or more of an ECG sensor, an SpO2 sensor, a heart rate sensor and a temperature sensor and a system can be configured to sense at least three vital signs simultaneously. In at least one embodiment, a sensor module can include two or more of an ECG sensor, an SpO2 sensor, a heart rate sensor and a temperature sensor and a system can be configured to sense at least two vital signs simultaneously.

Other and further embodiments utilizing one or more aspects of the disclosure described above can be devised without departing from the spirit of Applicants' disclosure. For example, while system 100 may be generally described in the context of being used for canines, this need not be the case and system 100 can alternatively or collectively be used for other animals. Further, the various embodiments of the present disclosure can be included in combination with each other to produce variations of the disclosed embodiments. Discussion of singular elements can include plural elements and vice-versa. The various steps described herein can be combined with other steps, interlineated with the stated steps, and/or split into multiple steps. Similarly, elements have been described functionally and can be embodied as separate components or can be combined into components having multiple functions.

Embodiments of the present disclosure have been described in the context of preferred and other embodiments and not every embodiment of the inventions has been described. Obvious modifications and alterations to the described embodiments are available to those of ordinary skill in the art having the benefits of the present disclosure. The disclosed and undisclosed embodiments are not intended to limit or restrict the scope or applicability of the inventions conceived of by the Applicants, but rather, in conformity with the patent laws, Applicants intend to fully protect all such modifications and improvements that come within the scope or range of equivalents of the following claims.

What is claimed is:

1. A system for monitoring animal vitals, comprising:
   a housing having a first side and a second side operable for coupling in direct contact with the skin of the animal and in sensing communication with the body of the animal;
   at least one sensor including an ECG sensor and an SpO2 sensor disposed at least partially within the housing and coupled with the second side of the housing for sensing one or more vital signs of the animal as sensor data including heart rate, SpO2, and respiration rate based on signals from the ECG sensor and the SpO2 sensor;
   a display module which converts the sensor data into human readable information, the display module having one or more graphical user interfaces (GUIs) including a BPM GUI which displays the human readable information indicative of the heart rate of the animal, and a SpO2 GUI which displays the human readable information indicative of the SpO2 of the animal, the one or more GUIs permitting a user to selectively choose which sensor in the at least one sensor to activate or deactivate;
   a controller disposed within the housing and operatively coupled to the at least one sensor for controlling the at least one sensor, the controller including one or more wireless modules to facilitate wireless communication with the display module, a first processor, and a first non-transitory machine-readable medium having instructions recorded thereon that, when executed by the first processor, cause the controller to:

cause the at least one sensor to acquire the sensor data indicative of the one or more vital signs of the animal, and cause a wireless transmission of the sensor data to the display module; and wherein the display module includes a display controller having a second processor and a second non-transitory machine-readable medium having instructions recorded thereon that, when executed by the second processor, cause the display controller to:

convert the sensor data into the human readable information;

cause a display of the human readable information via the display module;

calculate, in response to the sensor data, at least the respiration rate of the animal; and cause a wireless transmission of the calculation of at least the respiration rate to a remote user interface;

a database coupled to and accessible by the controller, the database comprising animal data that includes data representing normal vitals including heart rate, SpO2, and respiration rate based on a plurality of different animal species, age, breed, and sex;

wherein:

the BPM GUI facilitates entry by the user of a warning threshold heart rate value range for the animal;

the display controller determines whether the heart rate of the sensor data is within the warning threshold heart rate value range; and the display controller causes activation of at least one alarm when the display controller determines the heart rate of the sensor data remains within the warning threshold heart rate value range for a user determined period of time.

2. The system of claim 1, further comprising a clip configured to hold the at least one sensor in sensing communication with webbing of the animal's paw.

3. The system of claim 1, wherein the at least one sensor further comprises a heart rate sensor, a temperature sensor and a combination thereof.

4. The system of claim 1, wherein the data representing normal vitals comprises at least one of a minimum value and a maximum value input by the user.

5. The system of claim 1, wherein the display module is configured to display information regarding at least one of ECG, SpO2, heart rate, temperature, and respiratory rate based on input from the at least one sensor.

6. The system of claim 1, wherein the at least one alarm comprises at least one of a visual indicator, an audible indicator, and a mechanical indicator attached to the housing and electrically coupled to the controller, and wherein the system is configured to provide the user with at least one of the visual indication, the audible indication, and the mechanical indication in response to a presence or an absence of one or more conditions based on input from the at least one sensor.

7. The system of claim 1, wherein:

the SpO2 GUI facilitates entry by the user of an acceptable high SpO2 value and an acceptable SpO2 value for the animal;

the display controller determines whether a sensed SpO2 is within a range between the acceptable high SpO2 value and the acceptable low SpO2 value; and the display controller causes activation of the at least one alarm when the display controller determines the sensed SpO2 deviates from the acceptable low SpO2 value.

8. The system of claim 1, wherein:

the BPM GUI facilitates entry by the user of an acceptable high heart rate value and an acceptable low heart rate value for the animal;

the display controller determines whether the heart rate of the sensor data is within the acceptable high heart rate value and the acceptable low heart rate value; and the display controller causes activation of the at least one alarm when the display controller determines the heart rate of the sensor data deviates from the acceptable high heart rate value or the acceptable low heart rate value.

9. A system for monitoring animal vitals, comprising:

a housing;

at least one sensor including an ECG sensor and an SpO2 sensor disposed at least partially within the housing for sensing one or more vital signs of the animal as sensor data including heart rate, SpO2, and respiration rate based on signals from the ECG sensor and the SpO2 sensor;

a display module which converts the sensor data into human readable information, the display module having one or more graphical user interfaces (GUIs) including a BPM GUI which displays the human readable information indicative of the heart rate of the animal, the one or more GUIs permitting a user to selectively choose which sensor in the at least one sensor to activate or deactivate;

a controller disposed within the housing and operatively coupled to the at least one sensor for controlling the at least one sensor, the controller including one or more wireless modules to facilitate wireless communication with the display module, a first processor, and a first non-transitory machine-readable medium having instructions recorded thereon that, when executed by the first processor, cause the controller to:

cause the at least one sensor to acquire the sensor data indicative of the one or more vital signs of the animal, and cause a wireless transmission of the sensor data to the display module;

wherein the display module includes a display controller having a second processor and a second non-transitory machine-readable medium having instructions recorded thereon that, when executed by the second processor, cause the display controller to:

convert the sensor data into the human readable information;

cause a display of the human readable information via the display module;

calculate, in response to the sensor data, at least the respiration rate of the animal; and cause a wireless transmission of the calculation of at least the respiration rate to a remote user interface, at least one alarm disposed at least partially within the housing, the at least one alarm including at least one of a visual alarm, an audible alarm, a mechanical alarm, and a combination thereof; and a database that is coupled to and accessible by the controller, the database comprising animal data that includes data representing normal vitals including heart rate, SpO2, and respiration rate based on a plurality of different animal species, age, breed, and sex, the data representing normal vitals for the plurality of different species comprising at least one of a minimum value and a maximum value input by the user, wherein:

the BPM GUI facilitates entry by the user of a warning threshold heart rate value range for the animal;

the display controller determines whether the heart rate of the sensor data is within the warning threshold heart rate value range; and the display controller causes activation of the at least one alarm when the display controller determines the heart rate of the sensor data remains within the warning threshold heart rate value range for a user determined period of time.

10. The system of claim 9, wherein:

the BPM GUI facilitates entry by the user of an acceptable high heart rate value and an acceptable low heart rate value for the animal;

the display controller determines whether the heart rate of the sensor data is within a range between the acceptable high heart rate value and the acceptable low heart rate value; and the display controller causes activation of the at least one alarm when the display controller determines the heart rate of the sensor data deviates from the acceptable high heart rate value or the acceptable low heart rate value.

11. A system for monitoring animal vitals, comprising:

a housing;

a plurality of sensors including an ECG sensor and an SpO2 sensor disposed at least partially within the housing for sensing one or more vital signs of the animal as sensor data including heart rate, SpO2, and respiration rate based on signals from the ECG sensor and the SpO2 sensor;

a display module which converts the sensor data into human readable information, the display module having one or more graphical user interfaces (GUIs) including a SpO2 GUI which displays the human readable information indicative of the SpO2 of the animal, the one or more GUIs permitting a user to selectively choose which sensor in the at least one sensor to activate or deactivate;

a controller disposed within the housing and operatively coupled to the sensors for controlling the sensors, the controller including one or more wireless modules to facilitate wireless communication with the display module, a first processor, and a first non-transitory machine-readable medium having instructions recorded thereon that, when executed by the first processor, cause the controller to:

cause the at least one sensor to acquire the sensor data indicative of the one or more vital signs of the animal, and cause a wireless transmission of the sensor data to the display module;

wherein the display module includes a display controller having a second processor and a second non-transitory machine-readable medium having instructions recorded thereon that, when executed by the second processor, cause the display controller to:

cause a display of the human readable information via the display module;

calculate, in response to the sensor data, at least the respiration rate of the animal; and cause a wireless transmission of the calculation of at least the respiration rate to a remote user interface;

a database that is coupled to and accessible by the controller, the database comprising animal data that includes data representing normal vitals including heart rate, SpO2, and respiration rate based on a plurality of animal species, age, breed, and sex, the data representing normal vitals for the plurality of animal species comprising a minimum value and a maximum value for each of the normal vitals stored in the database, and data for canines and other species; and an alarm disposed within the housing and that provides at least one of an audible indicator and a visual indicator in response to the sensor data that is below the minimum value or above the maximum value, wherein:

the SpO2 GUI facilitates entry by the user of an acceptable high SpO2 value and an acceptable low SpO2 value for the animal;

the display controller determines whether the SpO2 of the sensor data is within a range of between the acceptable high SpO2 value and or the acceptable low SpO2 value; and the display controller causes activation of the alarm when the display controller determines the sensed SpO2 deviates from the acceptable low SpO2 value.

* * * * *